US007846658B2

(12) United States Patent
Laitala (10) Patent No.: US 7,846,658 B2
(45) Date of Patent: Dec. 7, 2010

(54) HOMOGENEOUS TIME-RESOLVED ENERGY TRANSFER ASSAY (75) Inventor: Ville Laitala, Turku (FI)

(73) Assignee: Wallac Oy, Turku (FI)

( * ) Notice: Subject to any disclaimer, the term of this patent is extended or adjusted under 35 U.S.C. 154(b) by 304 days.

(21) Appl. No.: 10/952,127

(22) Filed: Sep. 29, 2004

(65) Prior Publication Data
US 2005/0123957 A1 Jun. 9, 2005

Related U.S. Application Data (60) Provisional application No. 60/481,456, filed on Oct. 1, 2003.

(30) Foreign Application Priority Data
Jan. 30, 2004 (FI) ................................. 20045022

(51) Int. Cl.
C12Q 1/68 (2006.01)
G01N 33/53 (2006.01)
C12M 1/38 (2006.01)
(52) U.S. Cl. .................... 435/6; 435/7.1; 435/287.2; 436/172; 422/82.07; 422/82.08
(58) Field of Classification Search .............. 422/82.07, 422/82.08; 435/6, 7.1, 287.2; 436/172
See application file for complete search history.

(56) References Cited

U.S. PATENT DOCUMENTS

| 4,772,563 | A | * | 9/1988 | Evangelista et al. | ......... 436/518 |
| 5,656,433 | A | | 8/1997 | Selvin et al. | |
| 5,998,146 | A | * | 12/1999 | Latva et al. | .................... 435/6 |
| 6,218,124 | B1 | | 4/2001 | Lee | |
| 6,399,302 | B1 | * | 6/2002 | Lannigan et al. | ............... 435/6 |
| 7,067,275 | B2 | * | 6/2006 | Wolfbeis et al. | ............. 435/25 |
| 2002/0127688 | A1 | | 9/2002 | Burgess et al. | ............. 435/199 |
| 2002/0137027 | A1 | | 9/2002 | Durkop | |
| 2003/0099999 | A1 | | 5/2003 | Wei et al. | |
| 2003/0160151 | A1 | | 8/2003 | Zarate et al. | |
| 2004/0076979 | A1 | * | 4/2004 | Belik et al. | .................... 435/6 |
| 2005/0064485 | A1 | * | 3/2005 | Vogel | ............................. 435/6 |

FOREIGN PATENT DOCUMENTS

| EP | 0 973 036 A2 | 1/2000 |
| EP | 1 321 520 | 6/2003 |
| WO | WO 98/15830 | 4/1998 |
| WO | WO 02/41001 | 5/2002 |
| WO | 2004/086049 | 10/2004 |

OTHER PUBLICATIONS

Chen et al, Lifetime and color tailored fluorophores in the micro to millisecond time regime, 2000, J. Am. Chem. Soc., 122, 657-660.*

Blomberg et al, Terbium and rhodamine as labels in a homogeneous time resolved fluorometric energy transfer assay of the beta sub unit of human chorionic gonadotropin in serum, 1999, Clinincal Chemistry, 45, 855-861.*

Wang et al, Homogeneous time resolved fluoroimmunoassay of bensufuron-methyl by using terbium fluorescence energy transfer., 2001, Talanta, 55, 1119-1125.*

Malicka et al, Fluorescence spectral properties of cyanine dye labeled DNA oligomers on surface coated with silver particles, 2003, Analytical Biochemistry, 317, 136-146.*

Xiao et al., "An Improved Instrument for Measuring Time-Resolved Lanthanide Emission and Resonance Energy Transfer", Review of Scientific Instruments, Oct. 1999, pp. 3877-3881, vol. 70, No. 10, Physics Department and Biophysics Center, University of Illinois, Urbana, Illinois.

Vereb et al., "Temporally and Spectrally Resolved Imaging Microscopy of Lanthanide Chelates," *Biophysical Journal*, 1998, vol. 74, pp. 2210-2222, The Biophysical Society, Bethesda, Maryland, U.S.A.

Laitala et al., "Homogeneous Assay Based on Anti-Stokes' Shift Time-Resolved Fluorescence Resonance Energy-Transfer Measurement," *Analytical Chemistry*, 2005, vol. 77, pp. 1483-1487, American Chemical Society, Washington, D.C.

Laitala et al., "Homogeneous assay based on low quantum yield Sm(III)-donor and anti-Stokes' shift time-resolved fluorescence resonance energy-transfer measurement," *Analytica Chimica Acta*, 2005, vol. 551, pp. 73-78, Elsevier B.V., Amsterdam, Holland.

Qin et al., "Time-resolved Fluorescence Resonance Energy Transfer Assay for Point-of-Care Testing of Urinary Albumin," *Clinical Chemistry*, 2003, vol. 49, n. 7, pp. 1105-1113, American Association for Clinical Chemistry, Washington, D.C.

Ota et al., "Determination of interactions between structured nucleic acids by fluorescence resonance energy transfer (FRET): selection of target sites for functional nucleic acids," *Nucleic Acids Research*, 1998, vol. 26, n. 3, pp. 735-743, Oxford University Press, Oxford, U.K.

* cited by examiner

*Primary Examiner*—Stephen Kapushoc
*Assistant Examiner*—Narayan K Bhat
(74) *Attorney, Agent, or Firm*—Buchanan Ingersoll & Rooney PC (57) ABSTRACT

The invention relates to a method for improving the detection sensitivity in homogenous TR-FRET based bioaffinity assays. The sensitivity is improved by the use of long lifetime donors together with a high energy transfer efficiency and by carrying out the detection of the energy transfer based emission of the acceptor in a time window which is opened after a delay of 1 microsecond or more, but less than 50 microseconds, calculated from the donor excitation, and which time window has a width of 1 microsecond or more, but less than 100 microseconds. The invention concerns also the use of the improved method in multianalyte assays. Furthermore, the invention concerns a device suitable for carrying out the improved method.

8 Claims, 7 Drawing Sheets

HOMOGENEOUS TIME-RESOLVED ENERGY TRANSFER ASSAY

FIELD OF THE INVENTION

This invention relates to an improved homogeneous time-resolved energy transfer based bioaffinity assay, wherein the sensitivity is enhanced by increasing the signal/background ratio. The improved method is useful for detection of a single analyte, or for simultaneous detection of two or more analytes (multianalyte detection). The invention concerns also a device useful for carrying out the improved method.

BACKGROUND OF THE INVENTION

The publications and other materials used herein to illuminate the background of the invention, and in particular, cases to provide additional details respecting the practice, are incorporated by reference.

Förster type of non-radiative dipole-dipole energy transfer (Förster (1948) Ann. Physik., 6, 55) takes place between two molecules in condition where their energies (emission of donor (D) with absorption of acceptor (A)) overlap and they are located at a suitable distance from each other. The energy transfer requires a proper orientation of the oscillations of the molecules. The energy transfer efficiency E is given in the equation $E=1/(1+r^6/R_0^6)$, in which r means the distance between the donor and the acceptor, and $R_0$ is a distance parameter characteristic of the donor-acceptor pair and the medium between them. The usable distance scale for FRET experiments using conventional donor—acceptor pairs is ~10-100 Å.

Fluorescence resonance energy transfer (FRET), also called luminescence resonance energy transfer (LRET), has found extensive applications both in basic research and bioanalytical technologies as a platform for homogenous assays and as a spectroscopic ruler to measure distances in biomolecules. Ullman was the first to describe application of Förster type non-radiative energy transfer in homogenous bioanalytical assays based on antibody recognition reaction (Ullman, Scharzberg and Rubenstein (1967) J. Biol. Chem., 251: 4172) and a great number of suitable donor-acceptor probe pairs have since been developed and applied in immunoassays (for a review see I Hemmilä, Applications of Fluorescence in Immunoassays, Wiley, NY, 1991, chapter 8.3.4).

Time-resolved (TR) fluorometry (time resolution in time-domain at micro- or millisecond range) is an excellent measuring regime for homogenous assays because it can totally discriminate against ns-lifetime background fluorescence caused by organic compounds and light scattering. Suitable donors for TR-FRET measurements include among others lanthanide chelates (cryptates) and some other metal ligand complexes, which can have fluorescent lifetime in the micro-millisecond time region, and which therefore also allow the energy transfer to occur in micro-millisecond time region. This enables the time-resolved detection of the FRET-signal. Especially lanthanides and their fluorescent complexes have established a strong position as donors in TR-FRET measurements. Fluorescent lanthanide chelates have been used as energy donors already since 1978 by Stryer, Thomas and Meares (For example see Thomas et al. (1978) Proc. Natl. Acad. Sci., 75: 5746) and since a number of homogenous TR-FRET based assays have been described and patended (Mathis (1995) Clin. Chem., 41, 1391; Selvin et al. (1994) Proc. Natl. Acad. Sci., USA, 91, 10024) with their limitations and drawbacks.

Assay sensitivity has always been a critical parameter in bioassays. Very efficient way to measure a FRET based assay is to monitor the acceptor fluorescence instead of donor fluorescence. This is because in ideal circumstances the acceptor signal is specific only to the energy transfer (acceptors exited due to energy transfer) and the fluorescence signal is formed from only one fluorescent population, which makes the sensitive detection easier. Acceptor fluorescence monitoring also helps to avoid problems related to incomplete labeling of the FRET probes. In contrast the donor fluorescence basically always contains at least two different fluorescent populations: donors that participate in the energy transfer and free donors. Both populations emit at the same wavelength, which means that the change in the donor fluorescence signal is always measured against high background (free donors) in donor fluorescence channel.

Acceptor signal monitoring in FRET-assay has its own limitations, which are based on the energy transfer scheme of the probe pair and the fact that in most of cases the absorption of the acceptor overlaps with the emission of the donor (for non-overlapping energy transfer, see U.S. Pat. No. 5,998, 146). Therefore in photo-absorption based excitation methods the acceptor molecules will be excited directly by the donor excitation light to a degree proportional to the intensity of the external light source. Also due to the spectral overlap the excited donor always emits background fluorescence to the acceptor emission channel in some extent. The fluorescence signal resulting from these sources to the acceptor emission channel is non-specific to the energy transfer and limits the sensitivity in acceptor emission based FRET assays.

Methods to overcome these limitations has been described and patented. The use of temporal discrimination (long lifetime donor, short lifetime acceptor; and time-resolution) to avoid the effect of directly excited acceptor molecules was first described by Morrison (Morrison (1988) Anal. Biochem., 174, 101; U.S. Pat. No. 4,822,733). He used organic donor-acceptor pair; pyrene donor ($\tau$=400 ns) and phycoerythrin acceptor ($\tau$=4 ns). The effect of donor background fluorescence in acceptor emission channel can be reduced using donors with narrow emission bands, which enables more efficient optical filtering of the acceptor fluorescence. For example Selvin et al. have described significant improvements to S/B-ratio using europium- and terbium chelates as donors in TR-FRET measurements (Selvin et al. (1994) J. Am. Chem Soc., 116, 6029-6030; Selvin et al. (1994) Proc. Natl. Acad. Sci, USA, 91, 10024-10028). Mathis et al. used lanthanide cryptates, which have low overall quantum yield, as donors in TR-FRET assay to reduce the background caused by free donors (U.S. Pat. No. 5,512,493). Nevertheless there still exist a need for more sensitive FRET-assays.

Methods for homogenous FRET based multianalyte detection, in which more than one analyte can be detected simultaneously from the same assay medium, have also been described. The TAQMAN® method (Lee et al. (1993) Nucl. Acids. Res., Vol 21, 16, 3761-3766) uses dual labeled oligonucleotide probes, in which both the fluorescent reporter dye and the quencher are attached in the same oligonucleotide and TAQ-DNA polymerase cleavage of the probe causes the signal change in the assay. In TAQMAN® dual-assay the donors have different emission wavelengths and the donor signals are resolved by spectrally means. Molecular Beacon method (Tyagi S. and Kramer F. R. (1996) Nat. Biotech., 14, 303-308, U.S. Pat. No. 5,925,517) uses also dual labeled oligonucleotide probes, in which both fluorescent reporter dye and quencher are attached in the same oligonucleotide. The signal change is based on the self-hybridization of the probe. When the probe is not bound to the target the donor fluorescence is quenched due to the self-hybridization of the probe, which brings the reporter dye and the quencher in close proximity. When bound to target the self hybridization is avoided and the donor fluorescence can be obtained. In dual molecular beacon assay the donors have different emission wavelengths and the different donor signals are resolved by spectrally means. Hemmilä et al. have described a TR-FRET based homogenous multianalyte detection, in which separate donor-acceptor pairs are used for different analytes (WO 98/15830). The method is not described in detail but the donors are claimed to be lanthanide chelates (Eu, Tb, Sm) and acceptors are claimed to be short lifetime fluorophores. One can assume that the signal separation in the method described by Hemmilä is based either on spectrally resolvable donor emissions and/or spectrally resolvable acceptor emissions.

The problem related to optical signal separation methods is that usually the emission spectra of the suitable acceptor fluorophores are broad. It is difficult to totally avoid so-called crosstalk between the dye signals, which means that one dye also emits a certain percent of its total emission at the wavelength of a second dye. In high sensitivity assay this kind of crosstalk decreases the detection limit of the assay and can lead to false positive results, especially, if the one of the detected compounds has a large excess compared to the other compounds. Spectral crosstalk can be corrected mathematically afterwards, but it makes the data handling more difficult. Neither one of the methods described above is suitable for simultaneous multianalyte detection using one and the same donor for all analytes. Method described by Hemmilä (WO 98/15830) allows the use of one donor and different acceptors in multilabel assay but because of the spectral dependence of the energy transfer the suitable acceptors for the same donor have to have quite similar optical properties. This makes it difficult to avoid optically the crosstalk of different acceptor signals.

Conventional homogenous TR-FRET bioaffinity assays are usually based on the use of long lifetime lanthanide chelates as the donor molecules and organic chromophores (nanosecond lifetime) as the acceptor molecules. The lifetime of these lanthanide chelates is typically in the range of ~100-2500 μs depending on the chelate structure. The long lifetime of the donor (compared to the lifetime of free acceptor) allows the energy-transfer based acceptor signal to occur in the microsecond time region and this enables the time-resolved detection of the FRET based acceptor signal. Time-resolved detection (signal is integrated with certain delay time after the excitation pulse) in the microsecond time region eliminates efficiently the effect of nanosecond-lifetime background signal from the sample matrix and thus improves the signal/noise ratio (S/B-ratio) of the assay. Other benefit of lanthanide donors is that the emission spectrum of lanthanides consists of narrow peaks, which enables the spectral reduction (with optical filtering) of donor background in acceptor emission measurement channel. When measurement wavelength is selected suitably this allows additional improvement to S/B-ratio in acceptor emission based TR-FRET assays.

The ability to adjust the lifetime of the energy transfer based acceptor fluorescence by changing the energy transfer rate is not fully utilised in TR-FRET measurements and applications. Neither the ability to shorten the lifetime of energy transfer signal to a few microseconds when using ms-lifetime donor has been utilised in purpose to increase the TR-FRET assay sensitivity. For example the acceptor lifetime adjustment have been adapted in an application, in which so-called lifetime and colour tailored fluorophores have been developed (Chen and Selvin (2000) J. Am. Chem. Soc., 122, 657-660). In this application ms-lifetime donor and ns-lifetime acceptor are incorporated into a rigid template and the formed energy transfer complex with certain energy transfer efficiency is considered as a new single fluorophore, which can be further attached to molecule of interest. However, the acceptor lifetime adjustment is not used directly to optimise the TR-FRET measurement. In some published articles very short lifetime fluorescence signals (microsecond time scale) have been obtained in the acceptor measurement channel, when using millisecond lifetime donors and ns-lifetime acceptors, but the shortness of the signal has not been especially utilised in purpose to improve the assay sensitivity. In some particular cases the short lifetime acceptor population has been discarded during the TR data analysis based on the assumption that the short lifetime signal is caused by directly excited acceptor molecules or by a detector artifact (For example, see U.S. Pat. No. 5,656,433, Selvin et al (1994) J. Am. Chem Soc., 116, 6029-6030, Selvin et al (1994) Proc. Natl. Acad. Sci USA, 91, 10024-10028). Nevertheless directly excited ns-lifetime acceptor can not emit significantly in microsecond time scale due to very strong signal attenuation as a function of time. In addition to a detector artifact, also a high efficiency energy transfer process can produce very strong signal, which have a lifetime of few microseconds. With sophisticated TR instrument this type of phenomenon can be used to improve the sensitivity of TR-FRET assay.

There is a great need for TR-FRET assays with increased sensitivity for use in the detection of a single analyte, but particularly for use in multianalyte assays. The aim of the present invention is to overcome the limitations mentioned above.

SUMMARY OF THE INVENTION

The object of the present invention is to provide an improved homogeneous time-resolved energy transfer based bioaffinity assay, wherein the sensitivity is enhanced by increasing the signal/background ratio. This aim is achieved by increasing the energy transfer efficiency from the donor to the acceptor and by detecting the acceptor emission in a narrow time window after a short delay. Another object is to provide a method for simultaneous detection of two or more analytes, based on the improved homogeneous time-resolved energy transfer based bioaffinity assay. A further object is to provide an improved device capable of measuring the acceptor emission after a short delay.

Thus, according to one aspect, this invention concerns a homogeneous time-resolved luminescence energy transfer bioaffinity assay comprising a first group labelled with an energy donor and a second group labelled with an energy acceptor wherein the donor is a long excited state lifetime luminescent label and the acceptor is a short excited lifetime luminescent label and the change in energy transfer from the donor label to the acceptor label is measured. According to the invention, the detection of the energy transfer based emission of the acceptor is carried out in a time window which is opened after a delay of 1 microsecond or more, but less than 50 microseconds, calculated from the donor excitation, and in which the time window has a width of 1 microsecond or more, but less than 100 microseconds. The decay of the energy transfer based emission from the acceptor is essentially adjusted into said time window.

According to another aspect, this invention concerns a device useful for carrying out a homogeneous time-resolved luminescence energy transfer assay as defined above, wherein said device comprises a light source for the donor excitation, a detector for detecting the energy transfer based emission from the acceptor, an excitation filter, a dichroic mirror, sample, an emission filter, optical lenses, a counter and a data analyser. According to the invention, the background caused by the device is extinguished in less than 1 microsecond, calculated from the excitation light pulse.

According to a third aspect, the invention concerns a homogeneous time-resolved luminescence energy transfer bioaffinity assay comprising a first group labelled with an energy donor and a second group labelled with an energy acceptor wherein the donor is a long excited state lifetime luminescent label and the acceptor is a short excited lifetime luminescent label and the change in energy transfer from the donor label to the acceptor label is measured. According to the invention, at least two analytes are simultaneously detected, and each analyte is detected by a specific donor-acceptor pair, wherein the donors and/or acceptors for each analyte can be the same or different, and the acceptor emission decay times ($\tau_i$) for the different analytes (i) are different, and the whole decay curve of the acceptor emission signal is measured, and

- the lifetime equation $I(t) = \sum_i \alpha_i \exp\left(-\frac{t}{\tau_i}\right)$ where l(t) is the intensity of the mixture at a moment of time t, $\alpha_i$ and $\tau_j$ are the amplitude and corresponding lifetime of the i th fluorescent population in the measured curve, is fitted to the measured decay curve, and the different amplitudes $\alpha_i$ in the fitted equation are used to quantify the different analytes.

BRIEF DESCRIPTION OF THE DRAWINGS

FIG. 2B shows the relative intensity of the two acceptor signals plotted against the wavelength. The first analyte emits crosstalk to the optical channel of the second analyte but the crosstalk is avoided by the use of suitable TR window positioning. On the other hand, the second analyte emits crosstalk to the TR window of the first analyte (analyte-2 emission occurs at the same time scale with analyte-1 TR-window) but emission of the second analyte can be optically separated from the emission of the first analyte.

DETAILED DESCRIPTION OF THE INVENTION

This invention relates to a method and device for improving the detection sensitivity in homogenous TR-FRET based assays. It further relates to a method for carrying out a homogenous TR-FRET multilabel assay, in which more than one analyte can be detected simultaneously from the same medium with improved sensitivity. The methods described are applicable to TR-FRET assays where the donor and the acceptor form an energy transfer complex by binding specifically to the analyte, and the FRET based sensitized acceptor signal is then monitored.

In order to obtain a strong signal in TR measurement (energy transfer based acceptor emission in this case) it would be desirable to measure the energy transfer based emission after a minimised delay after the excitation pulse before the signal has remarkably decayed. Necessary (minimum) delay time in TR measurement is function of the background fluorescence lifetime. Normal background fluorescence (so-called autofluorescence) in bioassays is caused by organic materials and has typically a lifetime ~10 ns or less. A delay time of 1 µs is adequate to attenuate a 10 ns lifetime background by the factor ~2.7×10$^{43}$, which indicates that very short delays are theoretically usable in TR measurements. This aspect is however not utilised in conventional TR-FRET assays because commercial TR-instruments have limited performance when short delay times are used. Usually the shortest usable delay time is in the range ~10-100 µs, most often >50 µs, even though the instrument user interface allows the selection of very short delay time for the measurement. Performance is limited because with short delay times, especially 1-50 µs, the instrument background and other instrument related problems are increased, which makes the sensitive TR-detection not feasible and thus fast events in the 1-50 µs time scale can not be detected. This is partially the reason why the conventionally used TR-FRET chemistry is optimised to have signal lifetime in the range ~100-1000 µs, even though some advanced TR instruments on the market might be suitable for TR measurements using very short delay times.

Another aspect in TR-FRET acceptor emission measurement is the width of the TR window. Because of the spectral overlap principle of energy transfer the free donors typically emit background fluorescence also at the wavelength of acceptor emission. Additionally, the background signal of the free donors can not be discriminated by temporal means because of the long lifetime of the donors used in conventional TR-FRET assays. Suitable method for decreasing the level of obtained donor background is to shorten the width of the TR window. This aspect is however not fully utilised in conventional TR-FRET assays because the TR window has to be relatively wide to be able to integrate statistically adequate total signal from the assay.

In the case of long lifetime donor (microseconds) and short lifetime acceptor (nanoseconds), the lifetime of the FRET based acceptor signal is a function of the energy transfer efficiency, $E=1-\tau_{AD}/\tau_D$, (wherein E is energy-transfer efficiency, $\tau_{AD}$ is the lifetime or decay of the energy transfer based acceptor emission and $\tau_D$ is the lifetime of the donor emission). This means that the energy transfer efficiency in the conventional assays cannot be made very high (usually $E \leq 50\%$) without making the FRET-signal too fast for the instrument. When FRET signal has a lifetime ~100-1000 microseconds, delay time $\geq 50$ μs is usable in the measurement with conventional TR instrument because energy transfer signal is not totally quenched during the delay time. But due to the compromised energy transfer efficiency, the FRET based signal is not as high as possible and quite long signal integration time (TR window width ~100-1000 μs) or remarkably increased number of excitation pulses is required for statistically adequate total signal. The use of long TR window increases the amount of measured free-donor background in the assay. Additionally when energy transfer efficiency is compromised, despite the long integration time, a quite remarkably portion of the acceptor signal is anyway emitted outside the measurement window because the energy transfer process is slow. The so-called transmittance of the TR window (ratio: integrated signal in the TR window/integrated signal of the decay curve) is low in conventional TR-FRET assay.

Figure 1:
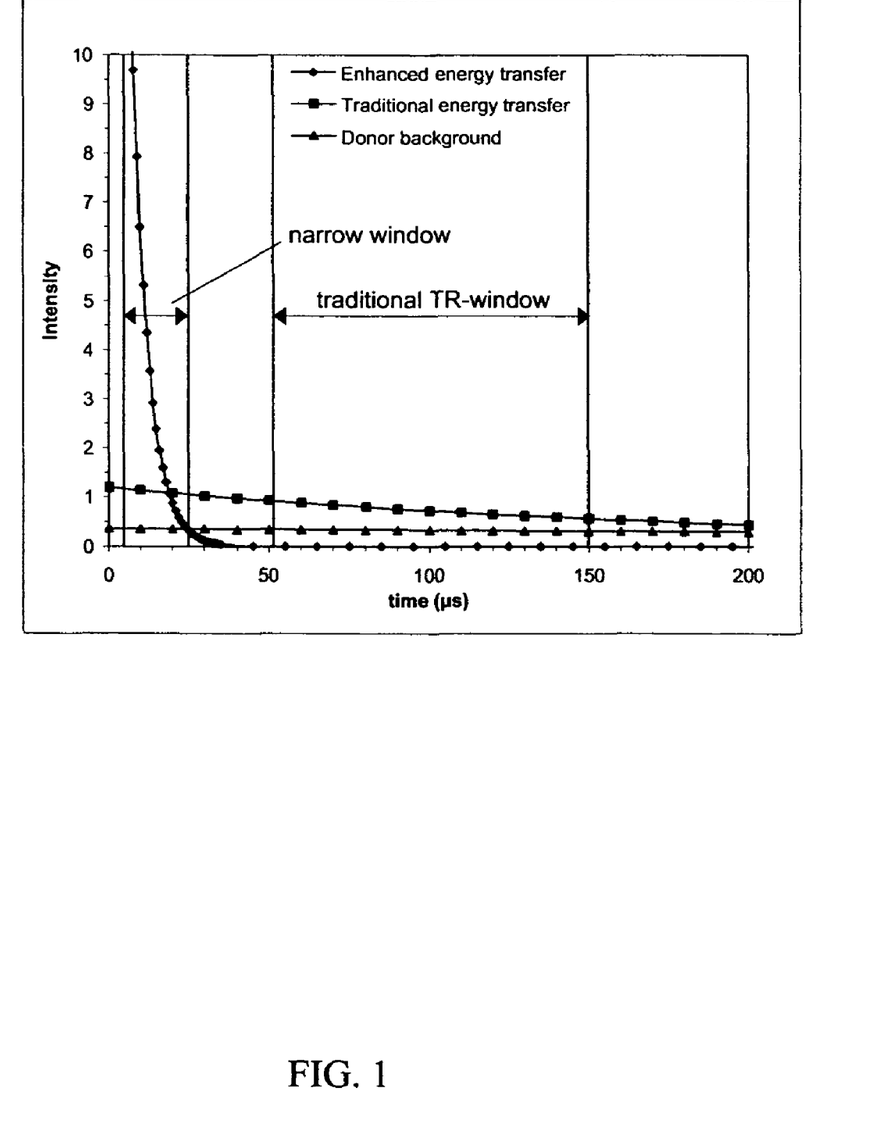
FIG. 1 shows the principle for the assay according to this invention, where the signal intensity is plotted against time. The comparison of a traditional TR-window to a narrow window according to this invention is shown. Explanation of curves: the curve denoted with diamonds is acceptor emission adjusted into the narrow window according to this invention; the curve denoted with rectangles shows an example of acceptor emission in traditional commercial TR-FRET assay and the curve denoted with triangles is the background from unbound donor.

Long lifetime donors (such as lanthanide chelates, lifetime ~1-5000 microseconds, preferably 1000-5000 microseconds) and short lifetime fluorophores as acceptors enable the FRET acceptor signal to occur in the microsecond time region, which allows the temporal discrimination of the nanosecond lifetime background signal and the signal of directly excited acceptor molecules with TR measurement. However, the donor background fluorescence in the acceptor emission channel (due to spectral overlap) always limits the sensitivity in FRET measurements and it can not be discriminated by temporal means. The main idea of this invention is to use long lifetime donors together with high energy transfer efficiency, and to carry out the TR-FRET measurements in a shortened (from about 100-1000 microseconds to about 1 up to 100 microseconds) time scale with a short delay time and a narrow measurement window. It should be emphasized, that the novel feature in the invention concerns a FRET dye pair, in which the donor lifetime is long ($\geq 1$ μs, preferably hundreds or thousands microseconds), and the detectable short lifetime acceptor signal is achieved using high energy transfer rate. It would be possible to achieve similar or shorter lifetime acceptor signals, as described in the invention, using short lifetime donor (lifetime less than few microseconds) and carrying out a lifetime based measurement (for example see Kang et al. (2002) J. Fluorescence, 12, 1, 97-103). Nevertheless, the described invention does not concern that kind of system and that kind of system does not offer the same kind of benefits as the method of the invention. Donor-acceptor population with high energy-transfer efficiency (E) (e.g. E>0.9) in the analyte specific complex produces enhanced sensitized acceptor signal due to increased probability of energy transfer. Importantly, the lifetime of the FRET based acceptor signal is dependent on the energy transfer efficiency and when the energy-transfer efficiency is high, the lifetime of the sensitized acceptor signal is remarkably shortened compared to the lifetime of the unquenched donor ($\tau_{acceptor}=(1-E)\tau_{donor}$). This enables one to take advantage of the usage of shortened time scale in the TR-FRET measurement. One main aspect of the invention is to adjust the decay of the acceptor signal to essentially fit into the shortened TR window by increasing the energy transfer efficiency suitably. With short delay and the narrow measurement window the measured energy transfer signal is increased due to better transmission of the TR window (ratio: integrated signal in the TR window/integrated signal of the decay curve) and due to increased probability of energy transfer. At the same time the amount of the detected long-lifetime donor background fluorescence, caused by the excited donor population without an acceptor nearby, is reduced as a function of the window length shortening. The longer the lifetime of the donor is, the lower is the background obtained (in short TR window) from certain population of free donors, because long fluorescent lifetime decreases the probability for a photon emission at a certain point of time. FIG. 1 shows the principle for the assay according to this invention, where the signal intensity is plotted against time. An example of a usable conventional TR-window and a narrow window according to this invention are shown. The detection sensitivity is improved by enhanced energy transfer and acceptor emission detection in a narrow window. In the narrow window the enhanced acceptor signal can be measured almost completely while the detected background signal is reduced. This improves the S/B-ratio compared to the traditional TR-FRET assay, in which the acceptor emission lifetime typically is in the range 100 to 1000 microseconds.

As shown in FIG. 1, the decay of the energy transfer based emission of the acceptor has been adjusted so as to essentially fit into the narrow (i.e shortened) time window. This condition is achieved adjusting the lifetime of the acceptor suitable by adjusting the energy transfer efficiency E from the donor to the acceptor according to the equation $\tau_{acceptor}=(1-E)\tau_{donor}$. The energy transfer efficiency can, in turn, be increased in many ways according to the Förster equation $E=1/(1+(r^6/R_0^6))$, where r means the distance between the donor and the acceptor, and $R_0$ is a distance parameter characteristic of the donor-acceptor pair and the medium between them ($R_0$ is a function of the D-A overlapping integral, donor quantum yield, refractive index of the medium and orientation factor between donor and acceptor dipoles). Thus, reducing the distance r between the donor and acceptor will lead to increased energy transfer efficiency. Alternatively, or in addition, the donor-acceptor pair can be chosen so that the distance parameter $R_0$, as defined in the Förster equation above, is increased. A high value of $R_0$ will also lead to increased energy transfer efficiency. Also other methods for increasing the energy transfer efficiency are known. For example, the presence of metal surfaces has been reported to affect the energy transfer efficiency (Lakowicz et al. (2003) J. Fluorescence, Vol. 13, No. 1, 69-77).

Preferably, the delay is 1 to 10 microseconds, more preferably 1 to 5 microseconds. The width of the time window is preferably in the range 1 to 50 microseconds, more preferably in the range 1 to 25 microseconds.

The donor is preferably a lanthanide chelate having an excited state lifetime of at least 100 microseconds. Especially suitable lanthanide chelates are disclosed in WO 98/15830 and references cited therein.

The acceptor is preferably a highly luminescent molecule with quantum yield as near unity (1) as possible and with high molar absorption coefficient, preferably over 100 000. The acceptor has to have energetic overlap with the donor, preferably the absorbtion of the acceptor has overlap with the energy-donating emission of the donor. A preferred feature of the acceptor is its sharp emission at a wavelength where the donor has minimum or does not have any emission. The lifetime of the acceptor shall be such that the emission of the directly excited acceptors should be totally decayed within 1 µs after the excitation pulse. Examples of suitable acceptors are disclosed in WO 98/15830 and the references cited therein but also many other acceptors are known in the art.

The improved assay according to the present invention is especially suitable for nucleic acid assays where the donor labelled probe and the acceptor labelled probe can be construed so as to give a very short, controlled, distance between the donor and the acceptor. However, this method is also applicable to other bioaffinity assays, provided that enhanced energy transfer efficiency between the donor and acceptor can be ensured.

Use of the Invention in Multianalyte Assays

Homogenous TR-FRET multianalyte assays become feasible by the use of separate specific donor-acceptor combinations for each analyte and by taking advantage of the ability to adjust the sensitized acceptor emission lifetime by adjusting the energy-transfer efficiency. The novel feature of the invention is to use one and the same donor molecule for multiple analytes and resolve the analyte spesific acceptor signals based on the signal lifetimes and optical filtering, in the case when different acceptors have partial optical crosstalk. This method totally discriminates against optical crosstalk of the acceptor labels, which is normally very presumable when the same donor is used for multiple analytes. However, if different acceptor signal can be totally resolved by spectral means the lifetime based signal separation is not necessary.

Figure 2:
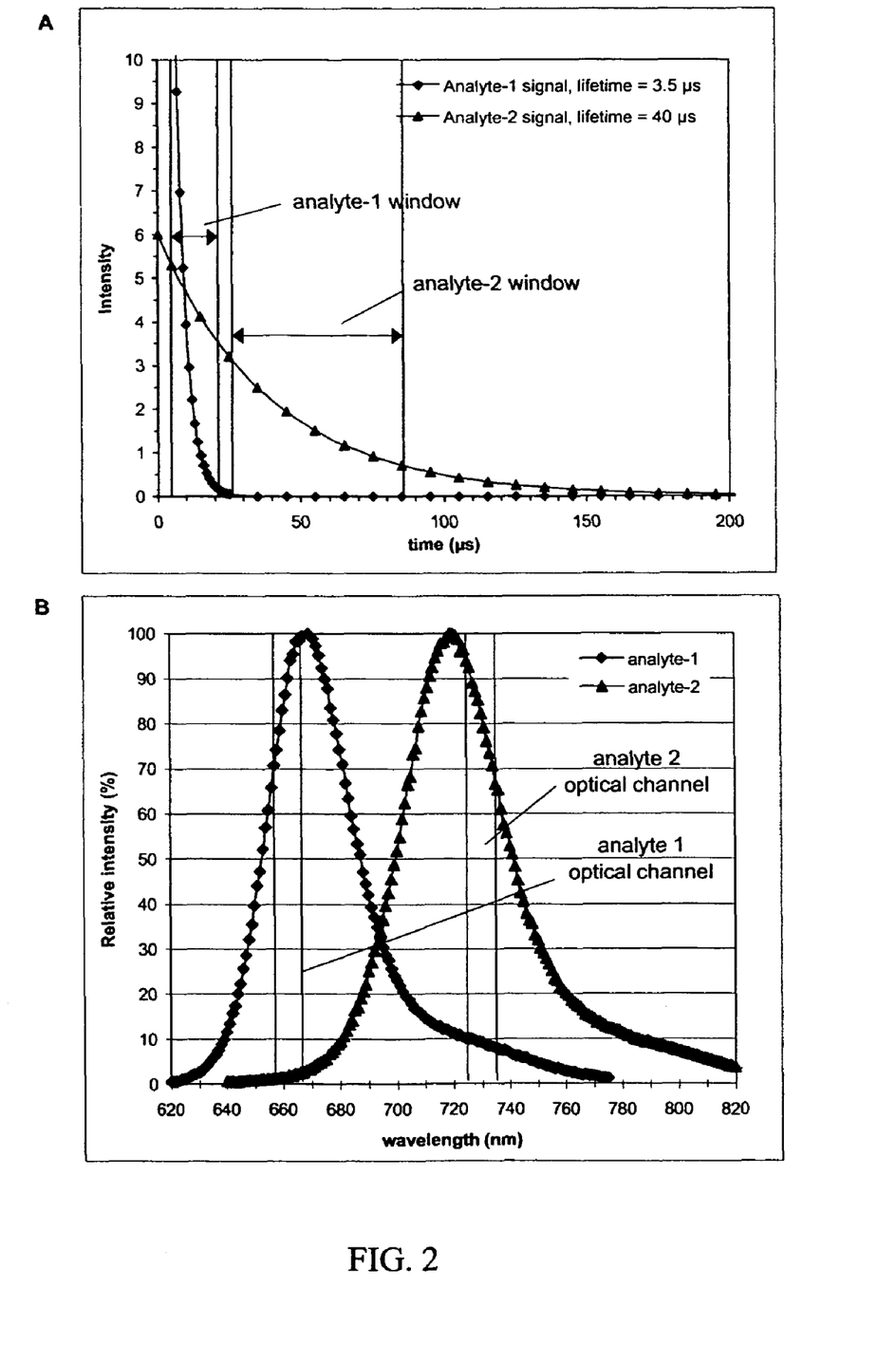
FIGS. 2A and 2B show the application of this method for simultaneous detection of two analytes and demonstrate the elimination of the optical crosstalk of the acceptor signals. The energy transfer emission from the acceptor of the first analyte is fitted into the narrow window opened after a short delay (diamonds). The lifetime of the energy transfer emission from the acceptor of the second analyte (triangles) is adjusted to be slightly longer than that of the first analyte and is detected in another TR window, opened at a moment when short lifetime acceptor signal of the first analyte has decayed (FIG. 2A).

For example, two analytes can be simultaneously detected with a donor-acceptor pair D-A1 for detection of the first analyte, and a donor-acceptor pair D-A2 for detection of the second analyte. The donor D could be different for the two analytes but it can also be the same. The energy transfer based emission of the first acceptor A1 is detected with short delay and the narrow time window according to this invention, while the energy transfer based emission of the second acceptor A2 is detected in a window, which is opened when A1 energy transfer signal has decayed (which can be before or after closing the TR window for A1 signal). Thus, different acceptor signals can be separated using simultaneously signal lifetimes and optical filtering. In a dual assay the analyte-1 acceptor signal lifetime can be adjusted to be short (e.g. lifetime <5 microseconds) by making the energy-transfer efficiency very high, and the detection sensitivity is improved with the narrow time window according to this invention. The lifetime of the analyte-2 acceptor signal is then adjusted to be slightly longer than that of analyte-1 (e.g. 25-50 microseconds) by the use of a suitable analyte-2 specific donor-acceptor combination and by keeping the energy-transfer efficiency still at a high level. Now, if the acceptors for analyte-1 and analyte-2 have partial optical crosstalk the analyte signals can be separated by a suitable positioning of the TR-measurement windows and by optical filtering. FIGS. 2A and 2B show the application of this method for simultaneous detection of two analytes, where signal separation is based on the fluorescence lifetime and optical filtering. Analyte-1 emits in the analyte-2 emission channel (FIG. 2B) but the crosstalk is eliminated using suitable TR measurement window for analyte-2 and measuring the analyte-2 emission when analyte-1 crosstalk has decayed (FIG. 2A). Analyte-2 emits in the analyte-1 TR measurement window (FIG. 2A), but the crosstalk is eliminated by optical filtering (FIG. 2B). No mathematical correction is needed. It is a common characteristic for fluorophores that emission spectrum of the fluorophore has a long red shifted tail after the emission maximum. The broad spectra make optical signal separation difficult even if fluorophores have emission maximums tens of nanometers apart from each other (for example, see FIG. 2B). When the same donor is used for many different acceptors it is very presumably that the optical crosstalk occurs between the acceptor signals. This is because different acceptors have to have quite similar properties to be able to participate in the energy transfer process with the certain donor.

In the multianalyte assay of this invention, analyte signals can also be separated based on fluorescence lifetime analysis. This is carried out by measuring the whole decay curve of the acceptor signal and by fitting the lifetime equation for the decay data. The time dependence for the overall fluorescence intensity of multiple excited populations, which have different emission lifetimes, can be expressed with multi-exponential equation [1]

$$I(t) = \sum_i \alpha_i \exp\left(-\frac{t}{\tau_i}\right) \quad [1]$$

where l(t) is the intensity of the mixture at a moment of time t, $\alpha_i$ and $\tau_i$ are the amplitude and corresponding lifetime of the i th fluorescent population in the measured curve. Basically equation [1] means that each fluorophore having different lifetime in the measured mixture causes its own exponential term to the decay curve of the mixture. The experimental decay data of the mixture can be fitted according to equation [1] and different amplitudes $\alpha_i$ in the fitted equation are proportional to concentrations of the fluorescent population having different lifetimes. With the multianalyte assay of this invention the different analytes can be adjusted to have clearly distinguishable acceptor emission lifetimes and the lifetimes can be pre-determined for each analyte. The pre-determined lifetimes are further used as constants when fitting the measured decay data of the analyte mixture. This kind of fitting procedure, in which the fitted lifetimes can be pre-determined, makes the fitting result of fluorescence decay curve more accurate because the number of fitted parameters is decreased compared to fitting of all the parameters in equation [1]. Additional benefit of fluorescence lifetime analysis is that different analytes can have their acceptor emission at the same wavelength and basically the acceptors can be same molecules for all analytes. Different lifetime of the analyte signals is the necessary requirement for carrying out the TR-FRET multianalyte assay in the case of fluorescence lifetime analysis.

Figure 3A:
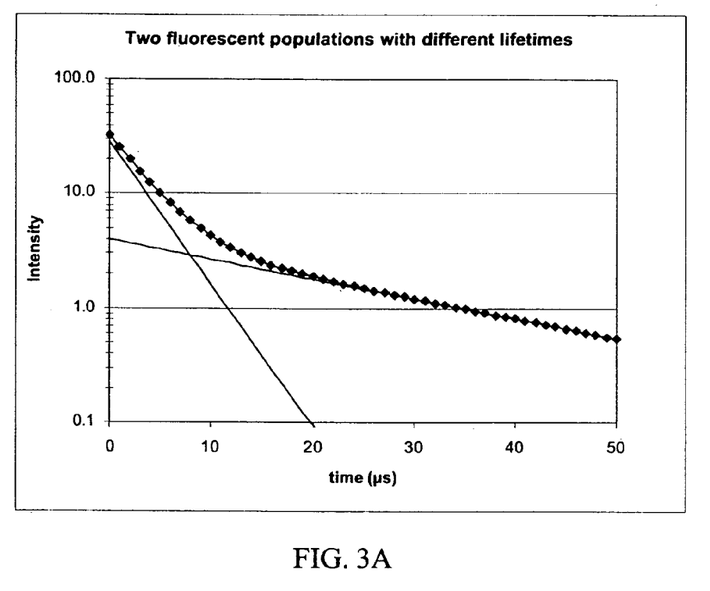
FIG. 3A shows decay curve simulation of two fluorescent populations having different lifetimes (3.5 µs and 25 µs) and which are emitting on the same wavelength (rectangles). For comparison, straight lines are the corresponding decay curves for the same fluorescent populations when they are measured alone. Both fluorescent populations cause their own exponential term to the summary decay curve.

If the acceptors have different emission wavelengths the decay curves for both analytes can be measured and fitted separately. An example of a decay curve, in which two excited fluorecent populations are emitting with different lifetimes, is illustrated in FIG. 3A.

The lifetime data can be measured for example with a multichannel scaler device, which has a certain number of data channels. The channels can be given a certain time length (e.g. 1 microsecond). Information on the excitation moment and the detector signal is given to the device. After the excitation moment the signal from the detector is during the first microsecond collected by channel 1. During the second microsecond the signal is collected by channel 2, etc. The signals collected by all the channels can be plotted versus time to obtain the decay curve of the measured signal. The time length of the channel defines the resolution of the decay data and the number of channels together with the time length of the channel defines the total time length of the measured decay data. For example with 1 μs resolution and 1000 channels the decay data is measured from 0 to 1000 microseconds. Preferably, the decay signal shall be collected during a time long enough so that the signal has extinguished completely. The end point of the collected data depends on the lifetime of the signal. It is preferable to collect data for a time about 5 to 10 times longer than the actual lifetime of the signal. Of this signal, a suitable set of data is fed to the processor and is used for curve fitting. In case the data contain errors, e.g. due to noise from the device, certain time points, i.e. certain channels can be omitted. It should be emphasized that also many other methods, different than the method described above, are suitable for obtaining the decay information of a fluorescence signal.

The assay according to this invention can also be used in a multianalyte assay detecting more than two analytes simultaneously. In this case the two first analytes can be detected as described above (also by using different donors for both analytes and using methods described above). The third and subsequent analytes can be further detected using the same donor, suitable acceptors and energy transfer rate, which enables the separation of different acceptor signals based on the principles described above. Preferably, the subsequent analytes are detected so that the next analytes always have a new donor for them. This makes it easier to find suitable, spectrally resolvable, acceptors and the eases the lifetime adjustment of every additional analyte. Energy transfer rate can be held at very high level for every analyte, which improves the detection sensitivity.

Figure 3B:
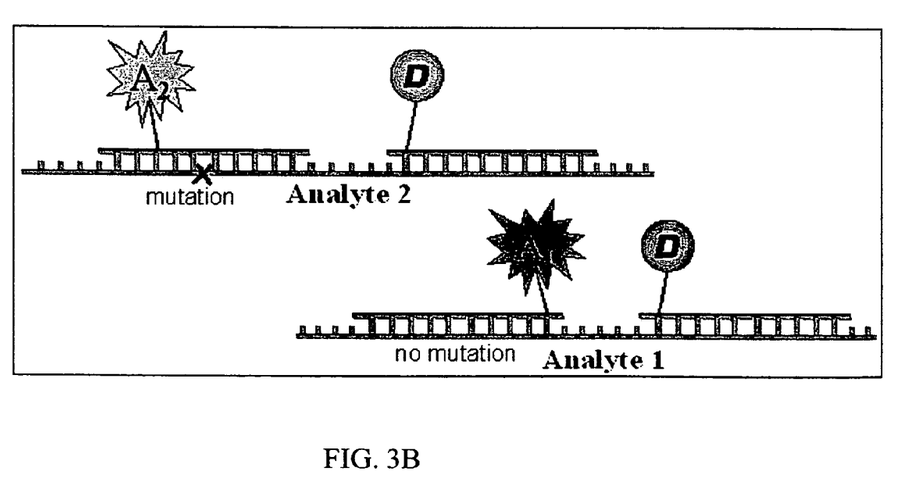
FIG. 3B illustrates the adoption of the method as a DNA assay for simultaneous detection of two different DNA sequences (mutated and non-mutated). The donor-acceptor distance and therefore the acceptor emission lifetimes are different for both analytes.

A model system for a dual TR-FRET DNA assay is illustrated in FIG. 3B. The donor labelled DNA probe binds to both of the analytes (single stranded DNA) and the two sequence specific probes recognize the mutated or non-mutated DNA sequences. The donor-acceptor distance and thereby the sensitized acceptor emission lifetime is slightly different for the two analytes. Acceptor signals can be measured without crosstalk by the simultaneous use of optical filtering and lifetime, as described in the invention.

Device for Carrying Out the Method According to this Invention

Figure 4:
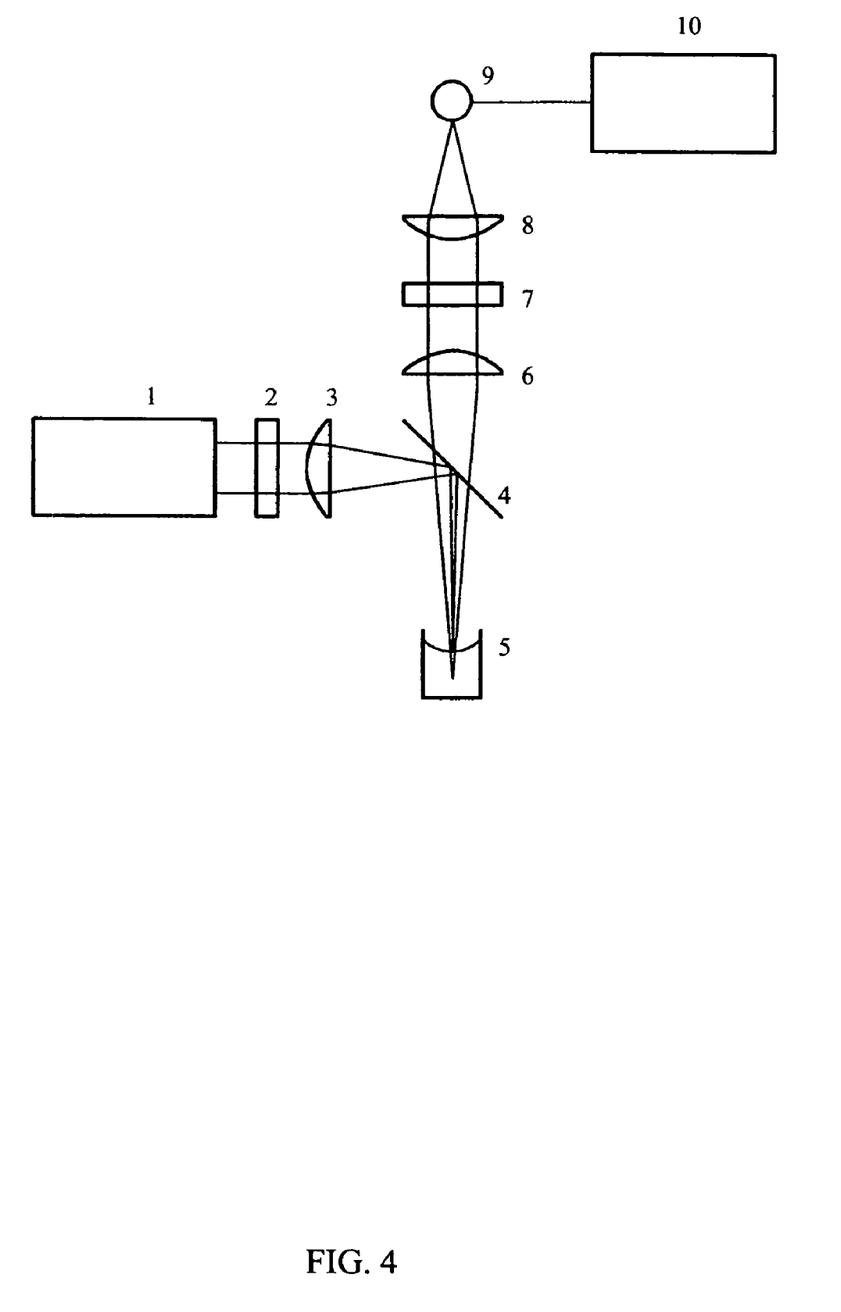
FIG. 4 shows an instrument setup for carrying out the method according to this invention.

An instrument setup useful for carrying out a homogeneous time-resolved luminescence energy transfer assay according to this invention is shown in FIG. 4. The device comprises an adjustable light source 1 for the donor excitation, excitation filter 2, lenses 3, 6 and 8 for refraction of the excitation and emission light, a dichroic mirror 4, sample holder 5, emission filter 7, a detector 9 for detecting the energy transfer based emission from the acceptor and a counter 10 for the processing of the detector signal. A short pulse of light is directed through excitation filter 2, lens 3 and dichroic mirror 4 to the sample 5. The donors in the sample absorb the light energy and are excited. The donors with acceptor in the nearby participate in energy transfer and the energy transfer based acceptor emission is transmitted through dichroic mirror 4, lenses 6 and 8, and emission filter 7 to the detector 9. The excitation filter 2, dichroic mirror 4 and emission filter 7 are selected suitably for the measured signal. A counter 10 is further used to measure the TR-signal for each acceptor in the selected TR window and/or to measure the decay curve of the emission. Essential is that the background caused by the device is shorter than 1 microsecond. Thus, specific TR instrumentation is needed to take full advantage of the method according to the invention. The main requirement is that the counting window can be opened in an adequate time scale (e.g. in microsecond scale) and with high resolution after the excitation pulse so that the short-lifetime acceptor signal can be detected with minimized level of instrument noise caused by the light source, optics and the TR detector system. This means that the instrument is equipped at least with a short pulse width light source (excitation pulse should be totally extinguished after 1 microsecond from the moment of excitation) and high quality optics (non-fluorescent) to reduce the instrument noise lifetime. Additionally, the detector system should be protected against the sample excitation pulse so as to overcome (e.g. with chopper, polarizer, gating or with some other method) the prompt fluorescence pulse (e.g. direct excitation light, fluorescence from optics, autofluorescence and other sources) hitting the detector at the instant moment of excitation without a rise in the detector noise. The TR detector should also be able to measure high rate photon flows in a narrow counting window without saturation of the detector.

An example of a useful light source for excitation of the donor is a laser such as a nitrogen laser, which extinguishes after about 10 nanoseconds in contrast to the traditionally used Xenon lamp, which needs about 10-40 microseconds for total extinction depending on the lamp type.

The invention will be illuminated by the following non-restrictive Examples.

EXAMPLES

Example 1

Adjustment of energy-transfer based acceptor fluorescence lifetime in homogenous FRET-assay for ΔF508 mutant DNA target.

The homogenous assay for ΔF508 mutant DNA was carried out using four different donor- and acceptor-probe combinations (table 1). These probe combinations allowed to carry out four different modifications of the same assay, in which the lifetime of the energy-transfer based acceptor signal is adjusted by the use of different donor-acceptor distances (D-A distances: 6, 8, 10 or 12 base pairs (bp) single stranded DNA).

TABLE 1

| Delta F508 target | 5' TTAAAGAAAATATCATTGGTGTTTCCTATGATGAATATAGATACAGAAGCGTCA 3' | (SEQ ID NO: 1) |
|---|---|---|
| WO1724-ALEXAFLUOR ® 647 | 3' Alexa647-modU-TACTTATATCTATGTCTTC 5' | (SEQ ID NO: 2) |
| WO1725-ALEXAFLUOR ® 647 | 3' Alexa647-modU-TATATCTATGTCTTCGC 5' | (SEQ ID NO: 3) |
| WO1726-Eu | 3' <u>AAA</u>TTATAGTAACCACAAA-Eu 5' | (SEQ ID NO: 4) |
| WO1727-Eu | 3' <u>AAATTT</u>TATAGTAACCACA-Eu 5' | (SEQ ID NO: 5) |

TABLE 1-continued

| D-A PAIR | D-A DISTANCE (BP) |
|---|---|
| WO1724-Alexa647 + WO1726-Eu | 6 |
| WO1724-Alexa647 + WO1727-Eu | 8 |
| WO1725-Alexa647 + WO1726-Eu | 10 |
| WO1724-Alexa647 + WO1727-Eu | 12 |

ΔF508 mutated target DNA and the specific probe sequences were synthesized using standard phosphoramidite chemistry (Expedite 8909 DNA-synthesizer, PerSeptive Biosystems) and were further purified using polyacrylamide gel electrophoresis (for gel electrophoresis details see Sambrook and Russel, Molecular cloning: a laboratory manual, 3$^{rd}$ edition, Cold Spring Harbor Laboratory Press, New York, 2001). The donor-probes were specific to the ΔF508 mutation in target DNA. The donor, W8044-Eu chelate (PerkinElmer Life and Analytical sciences, Wallac Oy, Finland), was attached to probe sequences using modified oligonucleotide blocks (Hovinen et al. (2001) Org. Letters, Vol. 3, No. 16, 2473-2476). The acceptor-probes were specific to the sequence near to the ΔF508 mutation site. The energy acceptor, ALEXAFLUOR® 647 (Molecular Probes Inc., Germany), was attached to probe sequence as a succinimidyl ester using amino modified oligonucleotide blocks (Hovinen et al. (2001) Org. Letters, Vol. 3, No. 16, 2473-2476). After labeling oligonucleotides were purified using polyacrylamide gel electrophoresis.

In the hybridization assays 5 nM ΔF508 DNA-target (or 0 nM ΔF508 DNA-strand in the blank sample) was incubated (2 h, RT) in detection mix containing 10 nM donor-probe and 10 nM acceptor-probe in 200 μl reaction buffer (15 mM TRIS, 2.5 mM MgCl$_2$, 50 mM KCI, 0.1% TRITON X-100). All four assay combinations (different D-A distances) were incubated in separate reaction tubes. After incubation 4 positive replicates and 12 blanks from each assay were pipetted to microwell plate (25 μl/well, 1508-0010 PerkinElmer Life and Analytical sciences, Wallac Oy, Finland). Time-resolved measurements were made on a laboratory build TR-fluorometer utilizing nitrogen laser (Oriel, USA, <10 ns pulse, 45 Hz), photomultiplier tube (Hamamatsu, Japan) and Turbo MCS multichannel scaler (EG&G) with 0.1 μs resolution. Energy transfer based emission (ALEXAFLUOR® 647) was collected through 665 nm emission filter (Omega Optical); 1000 excitation pulses were integrated per well. Lifetime data was fitted using Origin 6.0 (Microcal Software, Inc.) and gated signal was calculated from the MCS data using Microsoft Excel (Microsoft Corporation).

Results and Discussion

Fitted acceptor fluorescence lifetimes and theoretically calculated acceptor fluorescence lifetimes are shown in table 2. The obtained lifetime of the energy transfer based acceptor fluorescence depends on the D-A distance, which is an anticipated result according to the Förster's energy transfer theory. However, in this experiment, the distance dependence is not purely following the Förster's equations. The R$_0$ distance for W8044-Eu-ALEXAFLUOR® 647 donor-acceptor pair was determined to be 59.8 Å and theoretical acceptor signal lifetime can be calculated using equations [2] and [3] with the assumption that one base pair increases the length of the DNA strand by average 3.4 Å.

$$E=1/(1+r^6/R_0^6) \quad [2]$$

$$E=1-\tau_{AD}/\tau_D \quad [3]$$

in which r means the distance between the donor and the acceptor, R$_0$ is the critical energy transfer distance, $\tau_{AD}$ is the lifetime of the energy-transfer based acceptor signal and $\tau_D$ is the lifetime of the unquenched donor (1270 μs for W8044-Eu chelate in this experiment). Theoretical calculations contain a certain error because the possible effects caused by the linker arms (in amino modified block) and orientation of the energy transfer pair are ignored. Also the helical geometry of DNA chain has effect on the actual D-A distance. These effects are not taken into account in the theoretical calculation and the theoretical results should be considered only as a simplified example of theoretical signal behavior with certain error.

The clear result of the experiment is that the lifetime of the energy transfer based acceptor fluorescence can be tailored adjusting the D-A distance and it is possible achieve very high energy-transfer efficiencies above 90% (in this particular case E>99% in every assay model). The difference between obtained and theoretically obtained acceptor signal lifetimes is caused probably due to the flexibility of the single stranded DNA chain between the donor and the acceptor, which makes it difficult to estimate the true D-A distance change in the assay models.

TABLE 2

Obtained and theoretically calculated lifetimes of the energy transfer based acceptor fluorescence. E is calculated using equation [3] and the obtained acceptor lifetime ($\tau_D$ = 1270 μs).

| Length of single stranded DNA between D and A | Measured acceptor lifetime (μs) | Theoretical acceptor lifetime (μs) | E$_{obtained}$ |
|---|---|---|---|
| 6 | 2.1 | 2.0 | 0.998 |
| 8 | 3.5 | 11.1 | 0.997 |
| 10 | 4.9 | 41.5 | 0.996 |
| 12 | 8.4 | 116.4 | 0.993 |

Figure 5:
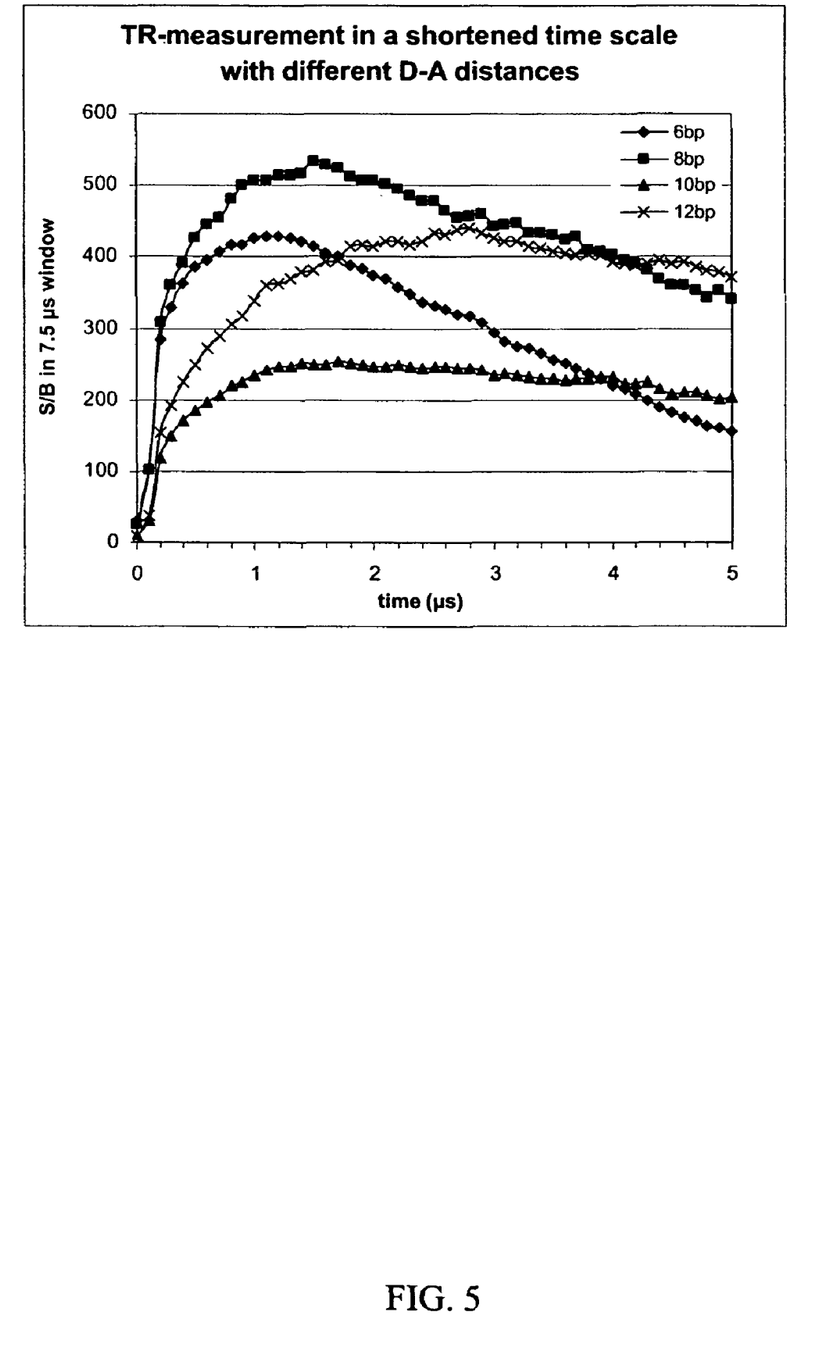
FIG. 5 shows the S/B ratio versus time for energy transfer based acceptor emission for various distances between the donor and the acceptor in a DNA assay.

The signal to background curves as a function of the TR-delay time are illustrated in FIG. 5 and this figure demonstrates the proof of principle of the short time scale TR-measurement. Very short time delay after excitation pulse (in this case 1-2 μs) is adequate to discriminate the ns-lifetime background of the assay (ns-background=directly excited acceptors, organic sample material, light scattering etc) and the S/B-curves reach their maximum shortly after excitation pulse. The performance variation between different assays in FIG. 5 is partially due to the selection of the TR window. The optimal TR-delay time and TR-window length (for optimal S/B-ratio) for an assay is dependent on the lifetime of the analyte signal but in this case the TR-window length was not separately optimized for the different assays models. Window length 7.5 μs was applied for every assay and the purpose of FIG. 5 is to demonstrate the suitability of shortened time scale for TR-FRET measurement. Measurement parameters and assays can be further optimized.

Example 2

Adjustment of Lifetime of the Energy-Transfer Based Acceptor Fluorescence by the Use of Different Spectral Overlap Factors The ability to change energy-transfer efficiency and the lifetime of the energy-transfer based acceptor fluorescence by changing the spectral overlap factor was demonstrated in a DNA double strand based FRET model system, which is illustrated in table 3. In model system W8044-Eu donor labeled DNA strand was hybridized with acceptor labeled DNA strand. Five different versions of the acceptor strand, which contained the same DNA-sequence but different fluorescent acceptor dye, were synthesized. After hybridization the D-A distance was the same in each sample but due to the different absorbtion properties of the acceptor dyes the spectral overlap factor with the donor and thereby the $R_0$ was different for every sample.

DNA sequences were synthesized using standard phosphoramidite chemistry (Expedite 8909 DNA-synthesizer, PerSeptive Biosystems) and were further purified using polyacrylamide gel electrophoresis (for gel electrophoresis details see Sambrook and Russel, Molecular cloning: a laboratory manual, $3^{rd}$ edition, Cold Spring Harbor Laboratory Press, New York, 2001). The donor, W8044-Eu chelate (PerkinElmer Life and Analytical sciences, Wallac Oy, Finland), was attached to DNA sequences using modified oligonucleotide blocks (Hovinen et al. (2001) Org. Letters, Vol. 3, No. 16, 2473-2476). The energy acceptors were from the Alexa dye series: ALEXAFLUOR® 647, 660, 680, 700 and 750 (Molecular Probes Inc., Germany). Acceptor dyes were attached to DNA sequences as a succinimidyl esters using amino modified oligonucleotide blocks (Hovinen et al. (2001) Org. Letters, Vol. 3, No. 16, 2473-2476). After labeling oligonucleotides were purified using polyacrylamide gel electrophoresis.

Three different samples were made for each measurement. Energy transfer sample: 10 nM Eu-strand and 50 nM acceptor-strand; non-energy transfer sample: 10 nM Eu-strand and 50 nM unlabeled acceptor-strand; Eu-control: 10 nM Eu-strand. Energy transfer efficiency was calculated based on the lifetimes obtained from the energy transfer sample ($\tau_{AD}$) and the non-energy transfer sample ($\tau_D$). Eu-control was measured to assure that the hybridization of the complementary strand to the Eu-strand does not remarkably affect to the lifetime of the donor.

laboratory build TR-fluorometer described in example 1. Energy transfer based emission was collected through 665 nm emission filter (ALEXAFLUOR® 647), through 730 nm emission filter (ALEXAFLUOR®s 660, 680, 700) or through 780 nm emission filter (ALEXAFLUOR® 750) using 1 µs MCS-resolution. All emission filters were from Omega Optical inc. 1000 excitation pulses were integrated per well and lifetime data was fitted using Origin 6.0 (Microcal Software, Inc.).

The effect of spectral overlap on lifetime of the energy-transfer based fluorescence is illustrated in table 4. It can be seen that the acceptor lifetime can be adjusted by changing the spectral properties (absorbtion) of the acceptor dye even though the physical D-A distance remains the same.

TABLE 3

| sequence |
|---|
| (SEQ ID NO: 6)<br>5' -Eu-TAAAGAAAATATCATCTTTGGTGTTTCCTATAA 3' |
| (SEQ ID NO: 7)<br>3' ATTTCTTTTATAGTAGA-ALEXAFLUOR ® 647 5' |
| (SEQ ID NO: 7)<br>3' ATTTCTTTTATAGTAGA-ALEXAFLUOR ® 660 5' |
| (SEQ ID NO: 7)<br>3' ATTTCTTTTATAGTAGA-ALEXAFLUOR ® 680 5' |
| (SEQ ID NO: 7)<br>3' ATTTCTTTTATAGTAGA-ALEXAFLUOR ® 700 5' |
| (SEQ ID NO: 7)<br>3' ATTTCTTTTATAGTAGA-ALEXAFLUOR ® 750 5' |

TABLE 4

| D-A pair | $\tau_{AD}$ (µs) | $E_{obtained}$ |
|---|---|---|
| Eu + ALEXAFLUOR ® 647 | 597.4 | 0.557 |
| Eu + ALEXAFLUOR ® 660 | 594.9 | 0.559 |
| Eu + ALEXAFLUOR ® 680 | 457.4 | 0.661 |
| Eu + ALEXAFLUOR ® 700 | 416.2 | 0.692 |
| Eu + ALEXAFLUOR ® 750 | 598.0 | 0.557 |

Example 3

Optimized Detection Sensitivity for ΔF508 Mutant DNA Target

Based on results from the example 1 the D-A distance 8 by was selected as the most suitable distance for shortened time scale TR-measurement in ΔF508 mutant DNA assay. Further, the donor and the acceptor probes were switched so that the Alexa 647 labeled probe (acceptor-probe) was now specific to the ΔF508 mutation site and the W8044-Eu labeled probe (donor probe) binds 8 base pairs next to the acceptor probe. Probe sequences are illustrated in table 5.

TABLE 5

| | | |
|---|---|---|
| Delta-F508 target | 5' TTAAAGAAAATATCATTGGTGTTTCCTATGATGAATATAGATACAGAAGCGTCA 3' | (SEQ ID NO: 1) |
| WO1705 | 3' AAATTTTATAGTAACCACA-ALEXAFLOUR ® 647 5' | (SEQ ID NO: 5) |
| WO1739 | 3' Eu-TACTTATATCTATGTCTTC 5' | (SEQ ID NO: 2) |

All samples were incubated (2 h, RT) in 500 µl reaction buffer (15 mM TRIS, 2.5 mM MgCl$_2$, 50 mM KCl, 0.1% TRITON X-100). After incubation 4 positive replicates of each sample were pipetted to microwell plate (50 µl/well, 1508-0010 PerkinElmer Life and Analytical sciences, Wallac Oy, Finland). Time-resolved measurements were made on a The probes were synthesized and labeled using methods described in example 1. Also now the hybridization conditions (NaCl-concentration, temperature and probe excess) and TR-measurement window (delay and window length) were optimized to obtain the best sensitivity for homogenous TR-FRET ΔF508 mutant DNA assay.

Dilution series of ΔF508 mutant target (3 nM, 1 nM, 0.3 nM, 0.001 nM) was prepared in hybridization buffer (15 mM TRIS, 100 mM NaCl, 2.5 mM MgCl$_2$, 50 mM KCl, 0.1% crosstalk between their emissions is illustrated in FIG. 2B (ALEXAFLUOR® 647 (diamonds), ALEXAFLUOR® 700 (triangles)).

TABLE 6

| | | | |
|---|---|---|---|
| Delta-F508 target | 5' TTAAAGAAAATATCATTGGTGTTTCCTATGATGAATATAGATACAGAAGCGTCA 3' | | (SEQ ID NO: 1) |
| W01705 | 3' AAATTTTATAGTAACCACA-ALEXAFLUOR ® 647 5' | | (SEQ ID NO: 5) |
| W01739 | 3' Eu-TACTTATATCTATGTCTTC 5' | | (SEQ ID NO: 2) |
| -2221ct target | 5' ACCCCACTACACGCTGCTGGGATCCTGGATCTCAGCTTCCCTGGCCGACAACACTGG | | (SEQ ID NO: 8) |
| | CAAACTCCTACTCATCCACGAAGGCCCTCCTGGGCATGGTGGTCCTTCCCAGCCTGGCA | | |
| | GTCTGTTCCTCACACACCTTGTTAGTGCCCAGCCCCTGAGGTTGCAG | | |
| | CTGGG GGTGTCTCTG AAGGG 3' | | |
| W01747 | 3' ALEXAFLUOR ® 700-GGGACCGGC 5' | | (SEQ ID NO: 9) |
| W01753 | 3' Eu-TGTTGTGACCGT 5' | | (SEQ ID NO: 10) |

Figure 6:
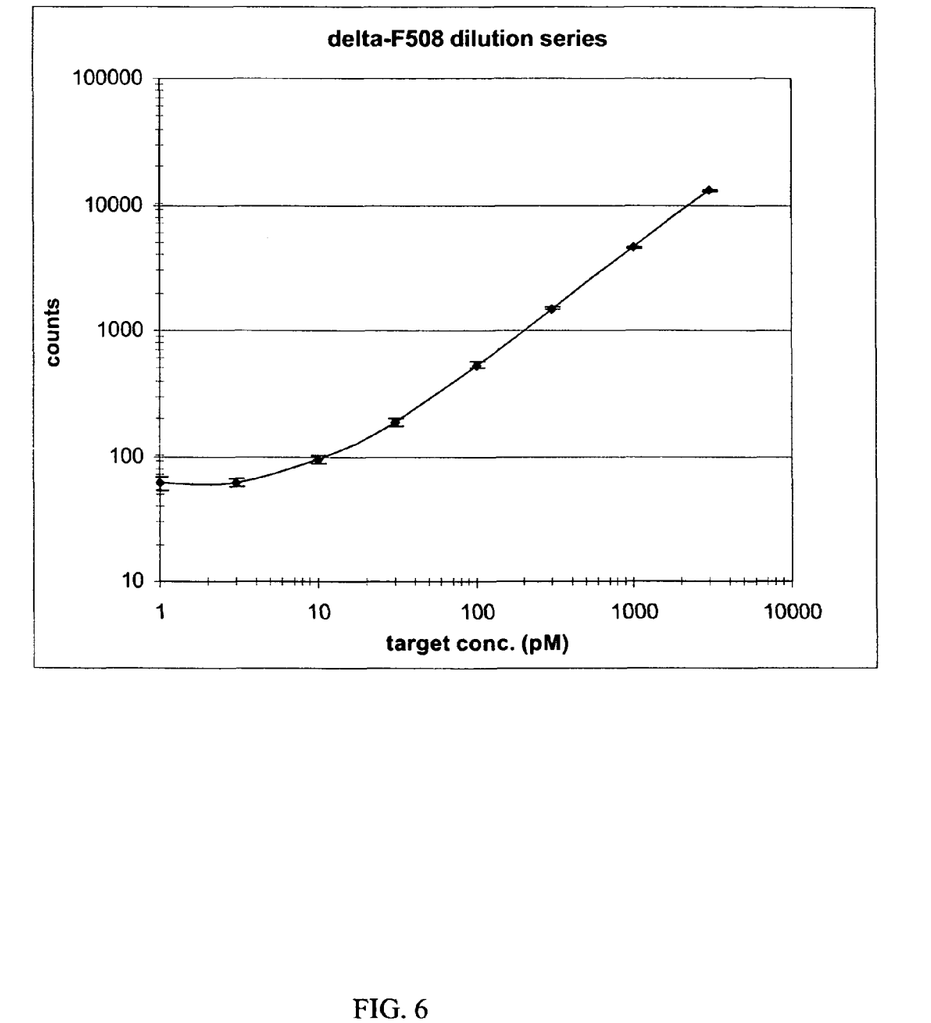
FIG. 6 shows the signal versus target concentration for delta-F508 dilution series.

TRITON X-100). Each sample from the dilution series was incubated (2.5 h, RT) in 150 μl detection mix containing 10 nM Alexa 647-probe and 10 nM W8044-Eu-probe in hybridization buffer. These hybridization conditions were optimized in separate measurements beforehand. After incubation 4 positive replicates and 12 blanks from each assay were pipetted to microwell plate (25 μl/well, 1508-0010 PerkinElmer Life and Analytical Sciences, Wallac Oy, Finland). Time-resolved measurements were made on a laboratory build TR-fluorometer described in example 1. Energy transfer based emission (ALEXAFLUOR® 647) was collected through 665 nm emission filter (Omega Optical). 1000 excitation pulses were integrated with 0.1 μs MCS-resolution and the TR-measurement result was calculated from the MCS data using TR-delay 2 μs and TR-window length 10 μs. Measurement curve for the dilution series is shown in FIG. 6. The detection limit of the assay is 7 μM ΔF508 mutant target (det. limit=avg(blank)+3*stdev (blank) and linear range of the assay continues at least up to 3 nM target concentration. For comparison, the detection limit for the same target in heterogeneous DELPHIA® assay is 2 μM. It can be concluded that the performance of the improved homogeneous FRET method of the invention is very similar to the DELPHIA® performance.

Example 4

Homogenous TR-FRET-Dual Assay: Proof of Principle

In this experiment the principle of TR-FRET based dual assay was demonstrated detecting simultaneously ΔF508 mutant DNA and −2221ct mutated DNA targets from the same assay medium. The sequence plan for TR-FRET dual assay is documented in table 6. The ΔF508 target and ΔF508 specific donor- and acceptor probes were the same as used in example 3. −2221ct target specific W8044-Eu donor-probe and ALEXAFLUOR® 700 acceptor-probe were synthesized and labeled using the methods introduced in example 1. The −2221ct target was first amplified (asymmetric PCR) from purified genomic DNA sample and further purified with MinElute PCR purification kit (50) (Qiagen) before hybridization. The spectra of both Alexa-dyes and the optical In the experiment both ΔF508 and −2221ct dilution series were first measured in single assays and the single-assay results were then compared to the dual assay result. Dilution series of the target DNA were prepared in hybridization buffer (15 mM TRIS, 100 mM NaCl, 2.5 mM MgCl$_2$, 50 mM KCl, 0.1% TRITON X-100). In single assays each sample of the dilution series was incubated (3 h, RT) in 200 μl detection mix containing. 10 nM target specific acceptor-probe and 10 nM target specific donor-probe. In dual assay ΔF508 and −2221ct samples were incubated (3 h, RT) simultaneously in 200 μl dual-detection mix containing 10 nM specific donor- and acceptor for both analytes. Corresponding dilutions in dual reaction tubes are documented in table 7. The −2221ct target dilutions were denatured (4 min+94° C., 2 min+4° C.) in each experiment before adding the −2221ct sample to the detection mix. Synthetic target ΔF508 was used without pretreatment. After incubation 4 positive sample replicates and 8 blanks from each assay were pipetted to microwell plate (25 μl/well, 1508-0010 PerkinElmer Life and Analytical Sciences, Wallac Oy, Finland). Time-resolved measurements were made on a laboratory build TR-fluorometer described in example 1. 1000 excitation pulses were integrated for every sample using 0.1 μs MCS-resolution. ΔF508 analyte signal was measured through 665 nm emission filter (Omega Optical) and data was analyzed using TR-delay 2 μs and TR-window length 10 μs. −2221ct analyte signal was measured through 730 nm emission filter (Omega Optical) and the data was analyzed using TR-delay 25 μs and TR-window length 30 μs.

TABLE 7

Corresponding target concentrations in a same well in dual assay

| sample | ΔF508 (nM) | −2221 ct (nM) |
|---|---|---|
| 1 | 1 | 30 |
| 2 | 0.3 | 10 |
| 3 | 0.1 | 3 |
| 4 | 0.03 | 1 |
| 5 | 0.01 | 0.3 |
| 6 | 0.003 | 0.1 |

Figure 7:
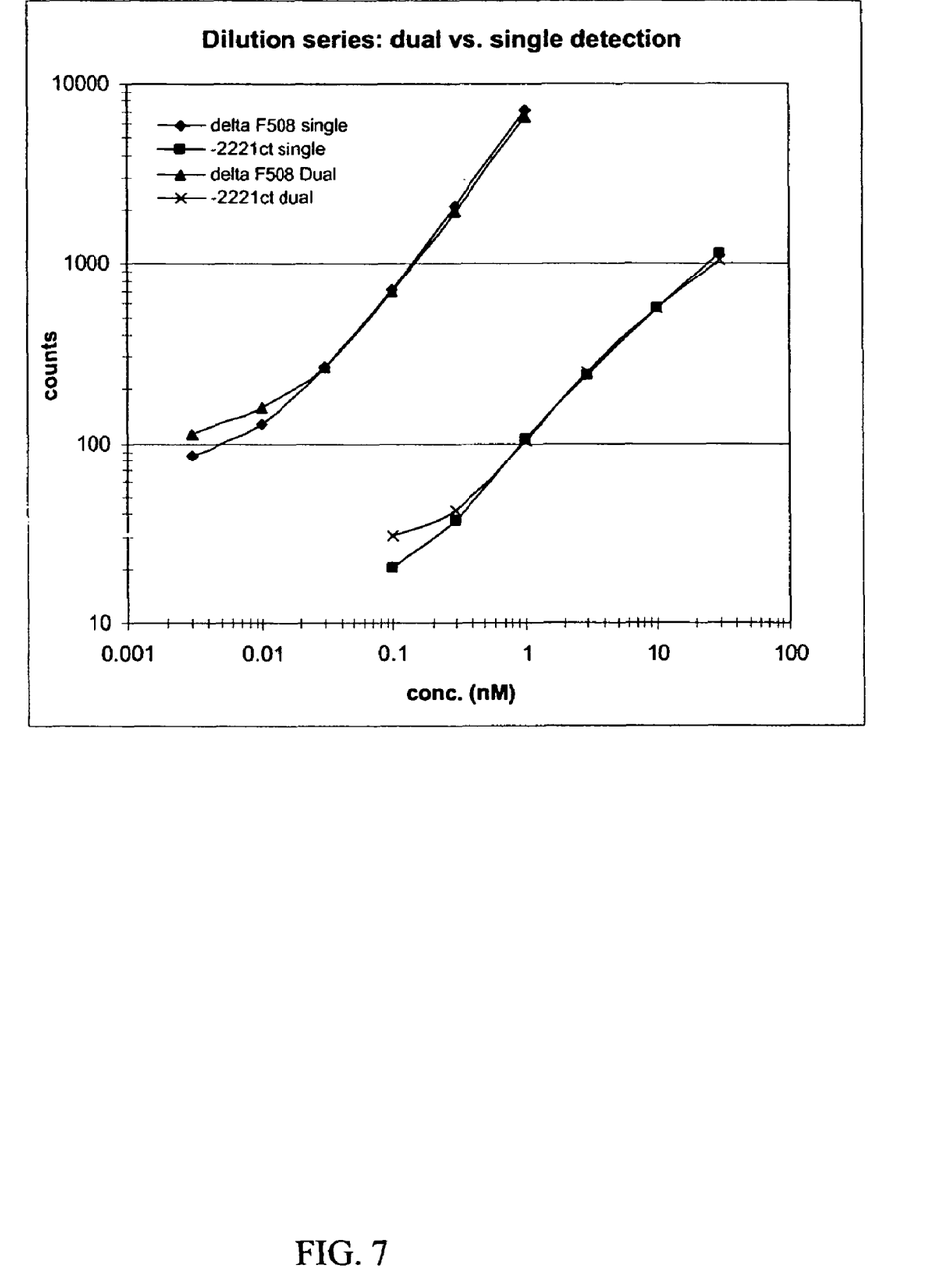
FIG. 7 shows the signal versus concentration for dilution series of delta F508 and −2221ct analytes as single detections and as dual detections.

Measured assay curves and dual-assay vs. single-assay comparison is documented in FIG. 7. The dual assay results are identical to single assay results with both ΔF508 and −2221ct analytes, which can be clearly considered as a proof of principle for the TR-FRET dual assay method. The partial optical crosstalk of the acceptors is eliminated using the methods described in the invention. For both analytes, the little difference between the dual and single curves at the lowest concentrations can be explained by the assay structure. In single assay case only one type of donor probes are present in the detection mix, and in this experiment the total Eu-probe concentration in single assay is 10 nM. However, the dual assay of the experiment requires separate donor-probes for both the analytes and the total Eu-probe concentration in dual assay is 20 nM. Due to the spectral overlap a part of the Eu-emission is always collected through acceptor emission filter and the Eu-concentration difference causes that the Eu-background of the measurement is doubled in dual assay. This signal increment can be seen near the detection limit where the actual assay counts are very low.

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

The invention claimed is:

1. A homogeneous time-resolved luminescence energy transfer bioaffinity assay comprising:

(a) providing a first molecule labelled with an energy donor, wherein the donor is a long excited state lifetime luminescent label, and a second molecule labelled with an energy acceptor, wherein the acceptor is a short excited lifetime luminescent label;

(b) allowing the first and second labelled molecules to form a complex, wherein energy transfer efficiency from the donor label to the acceptor label is E>0.9, when calculated using the decay time of the energy transfer based acceptor emission and the decay time of free donors; and (c) measuring the energy transfer from the donor label to the acceptor label, wherein the measuring comprises detecting the energy transfer based emission of the acceptor in a time window which has a width of 1 microsecond or more, but less than 100 microseconds.

2. The assay according to claim 1, wherein the width of the time window is in the range 1 to 50 microseconds.

3. The assay according to claim 1, wherein the donor is a lanthanide chelate having an excited state lifetime of at least 100 microseconds.

4. The assay according to claim 1, wherein at least two analytes are simultaneously detected, wherein each analyte is detected by a specific donor-acceptor pair.

5. The assay according to claim 4, wherein at least two analytes are simultaneously detected with a donor-acceptor pair D-A1 for detection of the first analyte, and a donor-acceptor pair D-A2 for detection of the second analyte, wherein the donor D is the same or different for said donor-acceptor pairs and that the energy transfer based emission of the first acceptor A1 is detected in the window as defined in claim 1, and the energy transfer based emission of the second acceptor A2 is detected in a window which is the same or different from the window in which the first acceptor A1 is detected.

6. The assay according to claim 5, wherein more than two analytes are simultaneously detected, wherein the two first analytes are detected according to claim 5 and the third and subsequent analytes are detected by donor-acceptor pairs in which the donor is the same or different from the donor used for detecting the two first analytes.

7. The assay according to claim 1, wherein the time window is opened after a short delay of 1 microsecond or more, but less than 50 microseconds, calculated from donor excitation.

8. A homogeneous time-resolved luminescence energy transfer bioaffinity assay comprising:
(a) providing a first molecule labelled with an energy donor, wherein the donor is a long excited state lifetime luminescent label, and a second molecule labelled with an energy acceptor, wherein the acceptor is a short excited lifetime luminescent label;
(b) allowing the first and second labelled molecules to form a complex, wherein energy transfer efficiency from the donor label to the acceptor label is E>0.9, when calculated using the decay time of the energy transfer based acceptor emission and the decay time of free donors; and
(c) measuring the energy transfer from the donor label to the acceptor label, wherein the measuring comprises detecting the energy transfer based emission of the acceptor in a time window which has a width of 1 microsecond or more, but less than 100 microseconds, wherein the assay comprises exciting with a light source which is a laser.

* * * * *

SEQUENCE LISTING

<160> NUMBER OF SEQ ID NOS: 10

<210> SEQ ID NO 1
<211> LENGTH: 54
<212> TYPE: DNA
<213> ORGANISM: Artificial
<220> FEATURE:
<223> OTHER INFORMATION: Synthetic target

<400> SEQUENCE: 1
ttaaagaaaa tatcattggt gtttcctatg atgaatatag atacagaagc gtca        54

<210> SEQ ID NO 2
<211> LENGTH: 19
<212> TYPE: DNA
<213> ORGANISM: Artificial
<220> FEATURE:
<223> OTHER INFORMATION: Probe

<400> SEQUENCE: 2
tacttatatc tatgtcttc                                               19

<210> SEQ ID NO 3
<211> LENGTH: 17
<212> TYPE: DNA
<213> ORGANISM: Artificial
<220> FEATURE:
<223> OTHER INFORMATION: Probe

<400> SEQUENCE: 3
tatatctatg tcttcgc                                                 17

<210> SEQ ID NO 4
<211> LENGTH: 19
<212> TYPE: DNA
<213> ORGANISM: Artificial
<220> FEATURE:
<223> OTHER INFORMATION: Probe

<400> SEQUENCE: 4
aaattatagt aaccacaaa                                               19

<210> SEQ ID NO 5
<211> LENGTH: 19
<212> TYPE: DNA
<213> ORGANISM: Artificial
<220> FEATURE:
<223> OTHER INFORMATION: Probe -continued

```
<400> SEQUENCE: 5 aaatttata gtaaccaca                                                    19

<210> SEQ ID NO 6
<211> LENGTH: 33
<212> TYPE: DNA
<213> ORGANISM: Artificial
<220> FEATURE:
<223> OTHER INFORMATION: Probe

<400> SEQUENCE: 6
taaagaaaat atcatctttg gtgtttccta taa                                   33

<210> SEQ ID NO 7
<211> LENGTH: 17
<212> TYPE: DNA
<213> ORGANISM: Artificial
<220> FEATURE:
<223> OTHER INFORMATION: Probe

<400> SEQUENCE: 7 atttcttta tagtaga                                                      17

<210> SEQ ID NO 8
<211> LENGTH: 182
<212> TYPE: DNA
<213> ORGANISM: Homo sapiens

<400> SEQUENCE: 8
accccactac acgctgctgg gatcctggat ctcagctccc tggccgacaa cactggcaaa      60
ctcctactca tccacgaagg ccctcctggg catggtggtc cttcccagcc tggcagtctg     120
ttcctcacac accttgttag tgcccagccc ctgaggttgc agctgggggt gtctctgaag     180
gg                                                                   182

<210> SEQ ID NO 9
<211> LENGTH: 9
<212> TYPE: DNA
<213> ORGANISM: Artificial
<220> FEATURE:
<223> OTHER INFORMATION: Probe

<400> SEQUENCE: 9 gggaccggc                                                               9

<210> SEQ ID NO 10
<211> LENGTH: 12
<212> TYPE: DNA
<213> ORGANISM: Artificial
<220> FEATURE:
<223> OTHER INFORMATION: Probe

<400> SEQUENCE: 10
tgttgtgacc gt                                                          12
```